(12) United States Patent
Do et al.

(10) Patent No.: US 10,551,245 B2
(45) Date of Patent: Feb. 4, 2020

(54) SIMPLE MONOLITHIC OPTICAL ELEMENT FOR FORWARD-VIEWING SPECTRALLY ENCODED ENDOSCOPY

(71) Applicants: Canon USA Inc., Melville, NY (US); The General Hospital Corporation, Boston, MA (US)

(72) Inventors: Dukho Do, Malden, MA (US); Dongkyun Kang, Somerville, MA (US); Mitsuhiro Ikuta, Cambridge, MA (US); Guillermo J. Tearney, Cambridge, MA (US)

(73) Assignees: CANON U.S.A., INC., Melville, NY (US); THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/430,205

(22) Filed: Feb. 10, 2017

(65) Prior Publication Data
US 2017/0322079 A1    Nov. 9, 2017

Related U.S. Application Data

(60) Provisional application No. 62/294,628, filed on Feb. 12, 2016, provisional application No. 62/451,213, filed on Jan. 27, 2017.

(51) Int. Cl.
*G01J 3/02* (2006.01)
*A61B 1/00* (2006.01)
(Continued)

(52) U.S. Cl.
CPC ........ *G01J 3/0218* (2013.01); *A61B 1/00009* (2013.01); *A61B 1/00096* (2013.01);
(Continued)

(58) Field of Classification Search
None
See application file for complete search history.

(56) References Cited

U.S. PATENT DOCUMENTS 3,976,360 A   8/1976   Schroder
4,074,306 A   2/1978   Kakinuma et al.
(Continued)

FOREIGN PATENT DOCUMENTS

JP   2009-523574 A   6/2009
JP   2011-527930 A   11/2011
(Continued)

OTHER PUBLICATIONS

Zeidan, A., et al., "Miniature forward-viewing spectrally encoded endoscopic probe", Optics Express, Aug. 15, 2014, pp. 4871-4874, vol. 39, vol. 16.
(Continued)

*Primary Examiner* — Michael J Hess
(74) *Attorney, Agent, or Firm* — Canon U.S.A., Inc., IP Division

(57) ABSTRACT

Exemplary spectrally encoded probes are provided having forward view capabilities. These probes are configured such that the detection element comprises a plurality of light collecting components, where the distal ends at least partially surround the illumination element and the proximal ends form a linear array that is optically connected to a dispersive component.

23 Claims, 6 Drawing Sheets

(51) Int. Cl.
*A61B 1/05* (2006.01)
*A61B 1/06* (2006.01)
*A61B 1/07* (2006.01)
*G01J 3/18* (2006.01)
*G01J 3/28* (2006.01)
*G01N 21/27* (2006.01)
*H04N 5/225* (2006.01)
*A61B 1/045* (2006.01)
*A61B 1/005* (2006.01)

(52) U.S. Cl.
CPC ...... *A61B 1/00165* (2013.01); *A61B 1/00167* (2013.01); *A61B 1/045* (2013.01); *A61B 1/051* (2013.01); *A61B 1/0638* (2013.01); *A61B 1/0669* (2013.01); *A61B 1/07* (2013.01); *G01J 3/18* (2013.01); *G01J 3/2823* (2013.01); *G01N 21/27* (2013.01); *H04N 5/2256* (2013.01); *A61B 1/005* (2013.01); *G01N 2201/0866* (2013.01); *H04N 2005/2255* (2013.01)

(56) References Cited

U.S. PATENT DOCUMENTS

| | | |
|---|---|---|
| 4,264,127 A | 4/1981 | Schumacher et al. |
| 5,279,280 A | 1/1994 | Bacich et al. |
| 5,565,983 A | 10/1996 | Barnard |
| 6,341,036 B1 | 1/2002 | Tearney et al. |
| 6,485,413 B1 | 11/2002 | Boppart et al. |
| 6,661,513 B1 | 12/2003 | Granger |
| 6,831,781 B2 | 12/2004 | Tearney et al. |
| 6,858,859 B2 | 2/2005 | Kusunose |
| 7,003,196 B2 | 2/2006 | Ghiron |
| 7,342,659 B2 | 3/2008 | Horn et al. |
| 7,448,995 B2 | 11/2008 | Wiklof et al. |
| 7,796,270 B2 | 9/2010 | Yelin et al. |
| 7,843,572 B2 | 11/2010 | Tearney et al. |
| 7,859,679 B2 | 12/2010 | Bouma et al. |
| 8,045,177 B2 | 10/2011 | Tearney et al. |
| 8,145,018 B2 | 3/2012 | Shishkov et al. |
| 8,203,708 B2 | 6/2012 | Lee et al. |
| 8,289,522 B2 | 10/2012 | Tearney et al. |
| 8,780,176 B2 | 7/2014 | Yelin |
| 8,804,133 B2 | 8/2014 | Yelin et al. |
| 8,812,087 B2 | 8/2014 | Yelin et al. |
| 8,818,149 B2 | 8/2014 | Shishkov et al. |
| 8,838,213 B2 | 9/2014 | Tearney et al. |
| 9,254,089 B2 | 2/2016 | Tearney et al. |
| 2002/0114566 A1 | 8/2002 | Fairchild et al. |
| 2002/0145815 A1 | 10/2002 | Moriyama et al. |
| 2003/0142934 A1 | 7/2003 | Pan et al. |
| 2004/0147810 A1 | 7/2004 | Mizuno |
| 2005/0155704 A1 | 7/2005 | Yokajty et al. |
| 2006/0114473 A1* | 6/2006 | Tearney ............... A61B 5/0066 356/479 |
| 2006/0244973 A1* | 11/2006 | Yun ..................... A61B 5/0059 356/511 |
| 2007/0081236 A1* | 4/2007 | Tearney ............... A61B 5/0062 359/390 |
| 2007/0188855 A1 | 8/2007 | Shishkov et al. |
| 2007/0233396 A1 | 10/2007 | Tearney et al. |
| 2008/0013960 A1 | 1/2008 | Tearney et al. |
| 2008/0097225 A1 | 4/2008 | Tearney et al. |
| 2009/0141360 A1 | 6/2009 | Koyama |
| 2010/0210937 A1 | 8/2010 | Tearney et al. |
| 2011/0237892 A1 | 9/2011 | Tearney et al. |
| 2011/0275899 A1 | 11/2011 | Tearney et al. |
| 2012/0025099 A1 | 2/2012 | Yelin |
| 2012/0112094 A1 | 5/2012 | Kao et al. |
| 2012/0212595 A1 | 8/2012 | Parmar et al. |
| 2013/0012771 A1 | 1/2013 | Robertson |
| 2014/0275986 A1* | 9/2014 | Vertikov ............... A61B 5/061 600/424 |
| 2014/0285878 A1 | 9/2014 | Escutti et al. |
| 2014/0316255 A1 | 10/2014 | Garai et al. |
| 2015/0015879 A1* | 1/2015 | Papadopoulos ........ G02B 23/26 356/301 |
| 2015/0045622 A1 | 2/2015 | Shiskov et al. |
| 2015/0055137 A1* | 2/2015 | Brown ............... G01B 9/02091 356/479 |
| 2015/0216398 A1* | 8/2015 | Yang ..................... A61B 1/043 600/109 |
| 2015/0335248 A1 | 11/2015 | Huang et al. |
| 2015/0348287 A1* | 12/2015 | Yi ......................... G06T 11/003 382/131 |
| 2015/0377701 A1* | 12/2015 | Pawluczyk ........... G01J 3/0243 356/301 |

FOREIGN PATENT DOCUMENTS

| | | |
|---|---|---|
| JP | 2015-526135 A | 9/2015 |
| WO | 2014031748 A1 | 2/2014 |
| WO | 2014104405 A1 | 7/2014 |
| WO | 2015116939 A1 | 8/2015 |
| WO | 2015116951 A2 | 8/2015 |
| WO | 2015116974 A1 | 8/2015 |

OTHER PUBLICATIONS

Pitris, C., et al., "A GRISM-based probe for spectrally encoded confocal microscopy", Optics Express, Jan. 27, 2003, pp. 120-124, vol. 11, No. 2.

Yelin, D., et al., "Three-dimensional miniature endoscopy", Nature, Oct. 19, 2006, pp. 765, vol. 443.

Kang, D., et al., "Spectrally-encoded color imaging", Optics Express, Aug. 17, 2009, pp. 15239-15247, vol. 17, No. 17.

Yun, et al., "High-speed spectral-domain optical coherence tomography at 1.3 µm wavelength", Opt Express, Dec. 29, 2003, pp. 3598-3604, No. 11, vol. 26.

* cited by examiner

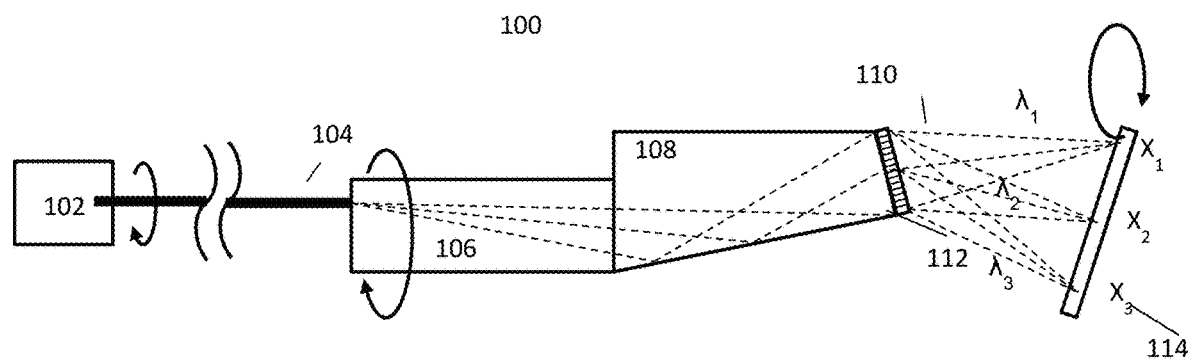
Fig. 1
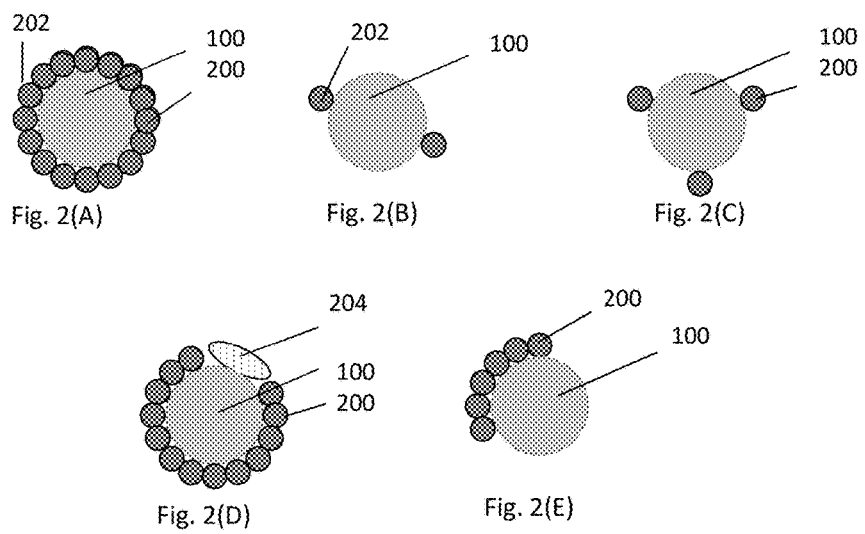
Fig. 2(A)  Fig. 2(B)  Fig. 2(C)
Fig. 2(D)  Fig. 2(E)
Figs. 2(A) – 2(E)

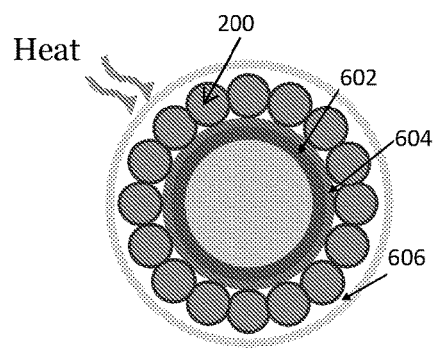
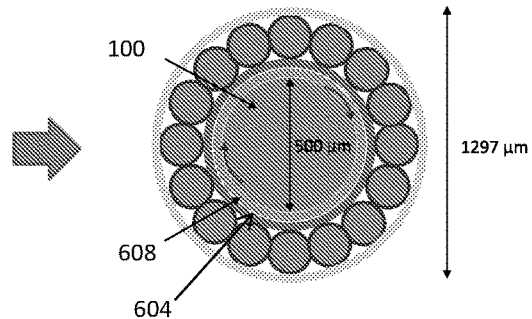
Fig. 6(A)              Fig. 6(B)
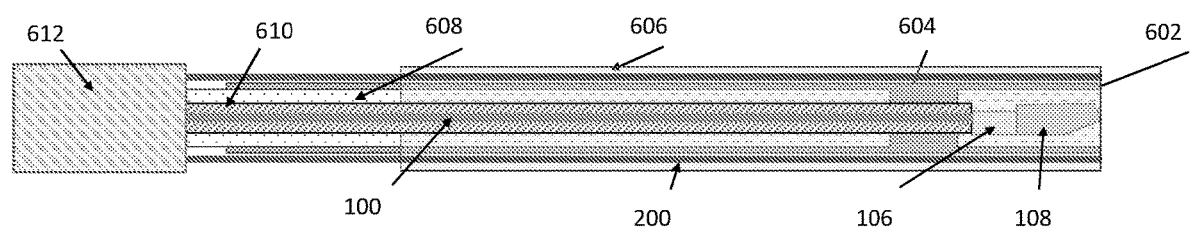
Fig. 6(C)

SIMPLE MONOLITHIC OPTICAL ELEMENT FOR FORWARD-VIEWING SPECTRALLY ENCODED ENDOSCOPY

CROSS-REFERENCE TO RELATED APPLICATIONS

This application claims priority to U.S. Provisional Application No. 62/294,628, filed Feb. 12, 2016 and to U.S. Provisional Application No. 62/451,213 filed Jan. 27, 2017 U.S. Provisional Application Nos. 62/294,628 and 62/451, 213 are hereby incorporated by reference in their entireties.

FIELD OF THE DISCLOSURE

The present disclosure relates generally to exemplary apparatus and method for endoscopy and, more particularly to exemplary spectrally encoded endoscopy probes for obtaining information of forward direction, exemplary methods for acquiring the image, and exemplary methods of making the endoscope.

BACKGROUND INFORMATION

Medical probes have the ability to provide images from inside the patient's body. Considering the potential damage to a human body caused by the insertion of a foreign object, it is preferable for the probe to be as small as possible. Additionally, the ability to image within small pathways such as small vessels, small ducts, small needles, cracks etc., requires a small probe size.

One useful medical probe employs a spectrally encoded endoscopy ("SEE"), which is a miniature endoscopy technology that can conduct high-definition imaging through a mm or sub-mm diameter probe. With SEE, broadband light is diffracted by a grating at the tip of the fiber, producing a dispersed spectrum on the sample. Light returned from the sample is detected using a spectrometer; and each resolvable wavelength corresponds to reflectance from a different point on the sample. The principle of the SEE technique and an SEE probe with a diameter of 0.5 mm, i.e., 500 µm have been described in D. Yelin et al., Nature Vol. 443, 765-765 (2006). SEE can produce high-quality images in two- and three-dimensions.

However, most SEE probes image the wall adjacent to the SEE probe and not the area in front of the probe. These side-view SEE configurations have some limitations, including a limitation of field angle by the grating, aberrations due to the cylindrical side wall of the probe, and that, in use, navigating the inside of organs is challenging without knowledge of what is in front of the probe.

Forward view SEE is preferable for many applications. Forward view SEE is particularly advantageous for applications such as orthopedics, ear, eye and sinuses (EENT), laparoscopy, and pediatric surgery.

One of the technical challenges for fabricating SEE probes has been to conduct forward-view SEE imaging (also called front-view SEE imaging). Previously, SEE probe designs that utilize double-prism grating prism (DP GRISM) have been proposed for forward-view imaging (see U.S. Pat. Pub. 2011/0237892, U.S. Pat. Nos. 8,145,018, and 7,796, 270, each of which are herein incorporated by reference as well as Zeidan et al., and Yun et al. (Optics Letters, 39(16): 4871-4, 2014; Optics Express, 11(2):120-4, 2003). While this publication demonstrated a spectrally-encoded confocal microscopy (SECM) and SEE probes there are numerous challenges in miniaturizing the probes to a size that is useable in SEE probe. Additionally, these probes are often challenged by either cross-talk between the excitation and detected light (e.g., when using a core/clad configuration for illumination and detection) or the loss of field of view (e.g., when using a separate fiber for detection).

However, there is still need for improved SEE optics and SEE systems, including improved signal level and the effective field of view. Accordingly, it can be beneficial to address and/or overcome at least some of the deficiencies indicated herein above, and thus to provide a new SEE probe that can view forward direction and an apparatus to use such a probe, e.g., for imaging in a small optics.

SUMMARY OF EXEMPLARY EMBODIMENTS

According to at least one embodiment of the invention, there is provided an probe comprising: an illumination element and a detection element. The illumination element comprise a light guiding component; a light focusing component; and a first dispersive component. The detection element comprises a plurality of light collecting components, such as multimode optical fibers, wherein the distal ends of the plurality of light collecting components at least partially surround the illumination element, a second dispersive component; a light focusing component; and a detector. The proximal ends of the plurality of light collecting components form a linear array that is optically connected to the second dispersive component. The plurality of light collecting components may form a ring around the illumination component at the distal end and form a line at the entrance slit to a spectrometer.

The invention further includes an system comprising a light source, a rotary junction, an illumination element, a detection element as described above, and a processer.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIG. 1 is a diagram of an embodiment showing illumination optics.

FIGS. 2(A)-2(E) are the end view of multiple embodiments of an optical probe.

FIGS. 6(A) and 6(B) are diagrams showing a cross-sectional view of the multi-MMF surrounding the illumination optics, where FIG. 6(A) is before the heatshrink process of multi-MMF sheath and FIG. 6(B) is after the heat shrinking. FIG. 6(C) shows a cross-sectional view in the opposite dimension of the illumination optics surrounded by the multi-MMF.

FIG. 9 is an exemplary image from a probe.

Figure 3:
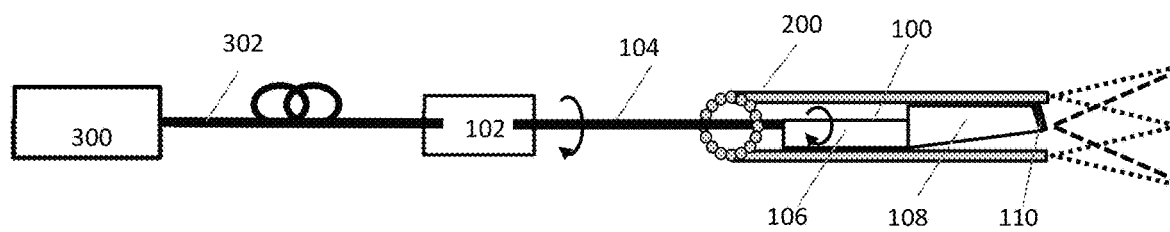
FIG. 3 is a diagram of an embodiment showing illumination and detection optics.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Illumination in a forward-view spectrally encoded endoscopic system may be done in one of several ways. For example, as shown in the embodiment of FIG. 1, light, after exiting a fiber rotary junction 102 is sent through an optical fiber 104. Light then enters a GRIN lens 106 which is rotated by the fiber rotary junction 102. Light then passes through a spacer element 108 which directs light to a stamped epoxy grating 110 after reflecting off a mirrored surface 112 of the spacer element 108. The grating 110 separates the light into the various wavelengths which are directed to a sample 114, where the various excitation wavelengths ($\lambda_1$, $\lambda_2$, and $\lambda_3$) imping on the sample at locations $\lambda_1$, $\lambda_2$, and $\lambda_3$. As the rotary junction 102 rotates the probe, the light on the sample also rotates, where light at position $\lambda_1$ makes a small diameter ring on the sample 114 and light at position $\lambda_3$ makes a ring having a larger diameter. While there may be a small area in the exact center of the sample 114, this probe allows for forward viewing. Other excitation optics may also be used. For example, the illumination optics described in WO 2015/116951, which is herein incorporated by reference, may be used.

In some embodiments, the illumination element provides light to a sample in a forward view configuration. Particularly, at least one diffracted light propagates from the grating component of the illumination element substantially along the probes optical axis, where the probe optical axis is the axis extending along the direction of propagation of a light provided from the light guiding component through the light focusing component. In some embodiments, the illumination element is configured such that, from the proximal end, a light from a broadband source will propagate from the light guiding component, through the light focusing component, off an optional light reflecting component, and then through or off the first dispersive component and onto a sample. The sample may be an in vivo sample, such as a tissue or organ.

Having more than one detection fiber and the fiber being a multimode fiber has the advantage of increasing light collection. That is, the more detection fibers, the greater the light collection. The multimode fiber has a larger core and will be advantageous in detection light coupling. For example, there may be 2, 3, 4, 5, 6, 7, 8, 9, to, 11, 12, 13, 14, 15, 16, 17, 18, 19, 20, 21, 22, 23, 24, or more detection fibers. A greater number of detection fibers is advantageous in that this provides a greater reduction in speckle and can increase the signal input into the detector. In some embodiments, the detection fibers may be packed closely in a ring around the illumination element. In some embodiments, the cladding around the distal end of the detection fibers is removed to increase the packing density of the detection fibers around the illumination element. Thus, the outer diameter of the illumination element-including any protective cladding not removed, limits the number of detection fibers that can form a fiber ring. For example, with a 50 µm tubing wall thickness for the illumination element, and 145 µm detection fiber diameter (including cladding), with a 6 µm tolerance, there can be 18 fibers surrounding the ring. For 185 µm detection fiber diameter (including cladding), with a 20 µm tolerance, there can be 14 fibers surrounding the ring. For the same detection fibers but with a 100 µm tubing wall thickness for the illumination element, there can be 20 and 15 fibers, respectively. In some embodiments, there may be two or three rows of rings around the illumination element.

Having more than one detection fiber will help in reducing speckles from the image because the detection fibers will be arranged at different position with respect to the illumination fiber, such that they collect light from the same point on the object with different optical path lengths. By separating multiple detection fibers apart as much as possible (but within the parameters needed for a small diameter probe), the speckle reduction effect will increase.

The light collecting components, which are exemplified as optical fibers (detection fibers) at least partially surround the illumination element. One way to separate the multiple detection fibers apart as much as possible and still work within the constraints of a cylindrical outer sheath is to arrange the multiple detection fibers in a ring around the illumination element. In one embodiment, the detection fibers 202 completely surround the illumination element 100 and form a fiber ring 200, as shown in FIG. 2(A). In other embodiments, several detection fibers 202 may be equally spaced around the illumination element 100 to form the plurality of light collecting components into the fiber ring 200, as shown in FIGS. 2(B) and 2(C). In other embodiments, as shown in FIG. 2(D), the plurality of detection fibers 202 surround most of the illumination element 100, but not completely, so as to have a space or a channel 204. This space or channel 204 can be used, for example, for one or more endoscopic tool(s). In other embodiments, the detection fibers 202 in the fiber ring 200 will not be equally spaced, and instead will have an unsymmetrical distribution around the illumination element 100 as shown in FIG. 2(E).

FIG. 3 demonstrates the forward view SEE detection optics. In this embodiment, a broadband source 300 provides light radiation in a wavelength range from about 420 nm to 820 nm. However, in other embodiments, other ranges, particularly those in the UV, visible, and IR may be used. In other embodiments, multiple radiation bands may be provided in one or more fibers to provide color SEE. A fiber 302 connects the broadband source 300 to the fiber rotary junction 102. Light then goes through an optical fiber 104, a GRIN lens 106 and then a spacer element 108 which has a grating 110 on the distal surface. Also shown is the collection optics that includes multiple detection fibers 202 forming a fiber ring 200 that encircle the optical elements of illumination element 100. This embodiment shows 16 multimode fibers in the fiber ring 200 that cover the entire field of view of the illumination optics, and is shown end-on in FIG. 2(A), where the detection fibers 202 form a ring 200 around the excitation optics part of the probe. The fiber ring 200 may optionally be encased or surrounded by an outer sheath (not shown) to protect the detection optics. This may be formed, for example, by using heat shrink tubing.

Figure 4:
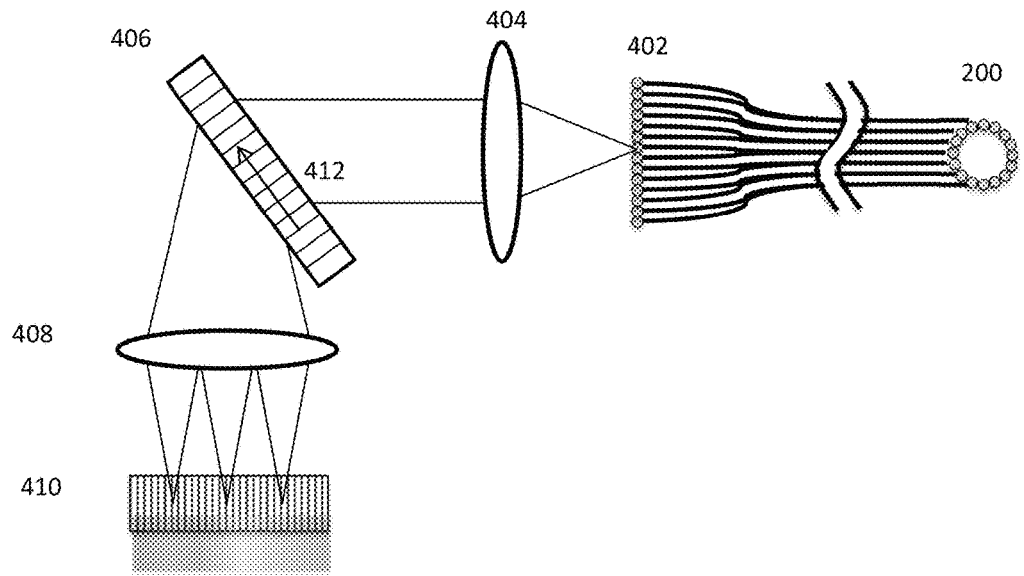
FIG. 4 is a diagram of an embodiment showing detection optics.

As shown in FIG. 4, after collection of the light from the sample through the fiber ring 200, the fiber ring 200 changes shape and becomes a linear array 402 of multimode fibers that terminate in a line. The linear array 402 of multimode fibers may be arranged, for example, as a single fiber thick (e.g., the 14×1) fiber array, as shown in FIG. 4. In other embodiments, the linear array may be two or more fibers thick. Light from this linear array 402 of multimode fibers is collimated by a collimation lens 404 and sent through a grating 406 and a focusing lens 408 before impinging on a lines scan camera 410.

The grating 406 has a grating vector 412 which is shown as an arrow on the grating. The collimating lens 404, grating 406, and focusing lens 408 may comprise a spectrometer where the linear array 402 of multimode fibers terminates at the spectrometer entrance. Other configurations of spectrometers may also be used in this invention. The linear array 402 of multimode fibers may cover the majority of (or the entire) entrance slit of the spectrometer. This will help in maintaining spectral resolution of the spectrometer utilizing the most of the collected light. The spectral resolution corresponds to image resolution in spectral encoded endoscope.

Figure 5:
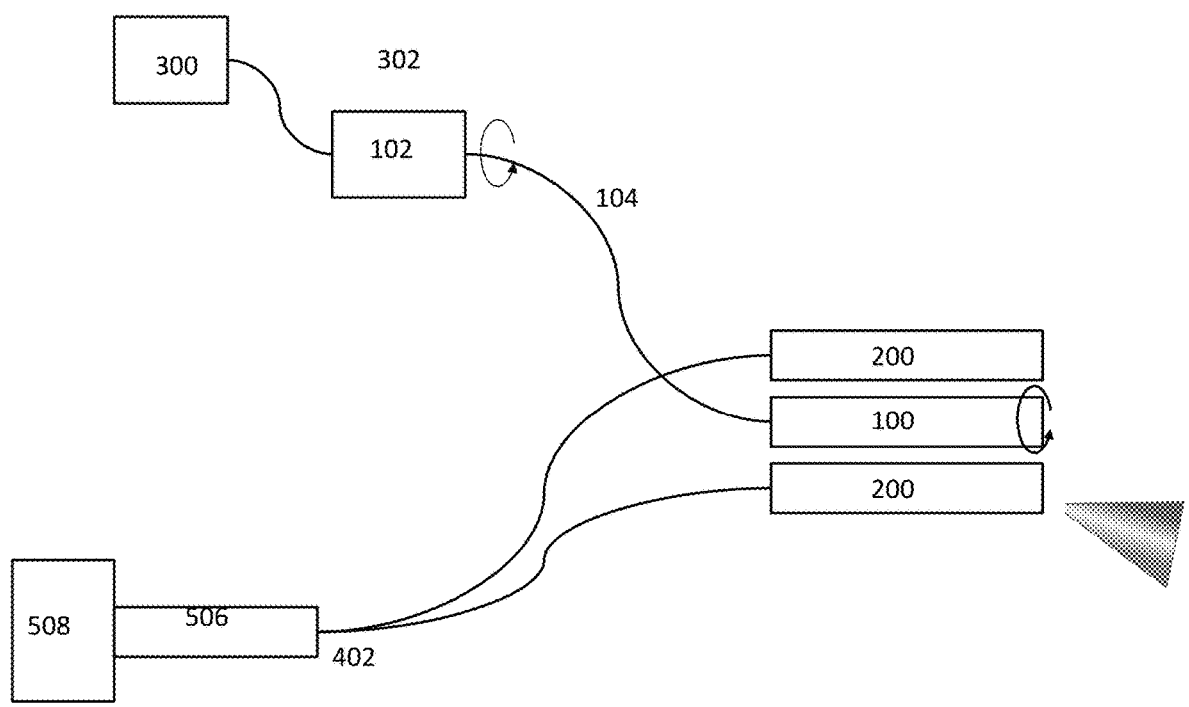
FIG. 5 is a schematic of a forward-view SEE system.

FIG. 5 demonstrates the system including the broadband source 300, and a fiber 302 connecting the broadband source 300 to the fiber rotary junction 102. Light goes through an optical fiber 104 to the illumination element 100. The rotation of the illumination element 100 is depicted with the circular arrow and the spectrum of light is incident on a sample (not shown). The detection element including the fiber ring 200 is shown as a cross-section, where light is sent through the multimode fibers and lined up in a linear array 402 at the entrance slit to a spectrometer 506. The light is then imaged on a detector 508.

In some embodiments, the detector 508 is a line scan sensor, such as a line scan camera. The line scan sensor may be a rectangular pixel element having longer dimension of the sensor pixels perpendicular to the grating vector 412 of the grating 406 in the spectrometer. It can also maintain spectral resolution by covering small wavelength width with a shorter dimension of the pixel in the opposite dimension; and collecting more light and improves in signal intensity by covering the lined up image of the fiber end with longer dimension of the pixel. The line scan sensor may be, for example, a single pixel wide, 2 pixels wide, 5 pixels wide, or more, as long as the line scan sensor is rectangular.

The illumination optics may be made, for example, by PDMS stamping on a fused silica grating. The grating may also be made by replica molding of the grating pattern on the SEE probe, where a UV-curing epoxy is used to stamp the grating onto the spacer element using a stamp and UV light. See, for example, WO2015/116974 and WO2014/031748.

The detection element may be made, for example, by fixing the detection fibers 202 around a tube that surrounds the illumination element. The illumination element may be inserted into the detection element after formation of the detection element by, for example, using hypotubing or another mandrel to keep the shape of the detection element during the formation. The detection fibers 202 are located around the perimeter of a tube and a heat shrink tubing may be fixed around the outer diameter of this ring of detection fibers to protect and hold the detection fibers. This process is shown in FIGS. 6(A) and 6(B) where an inner tubing (hypotube) 602 is inserted within a stationary tubing (i.e., a polyimide tubing) 604. After the fiber ring 200 (a plurality of multimode fibers) is placed, a heat shrink tubing 606 is placed around the probe. The illumination optics of illumination element 100 with a surrounding rotating tubing (i.e., a polyimide tubing) 608 are inserted within the stationary tubing 604 after removal of the hypotube 602. With an exemplary 500 μm illumination element 100 and 185 μm detection fibers 202, the overall diameter is 1297 μm. An exemplary probe having illumination element 100 inserted inside a rotating tube 602 where multi-MMF form a fiber ring 200 surrounding the optics of illumination element 100, rotating tube 608 and stationary tube 604 is shown in FIG. 6(C). This figure also shows the torque coil 610 and tube 612 surrounding the proximal portion of the probe assembly.

According to certain exemplary embodiments of the present disclosure, the exemplary SEE probe can facilitate a view in a forward direction, which can add an additional value to various endoscopy systems. For example, the SEE probe according to various exemplary embodiments of the present disclosure can be useful in in vivo applications. The exemplary probe(s) can be configured for use in vivo, and, with a small size thereof, provide advantage over other large conventional probes that can require a more complex and invasive procedure for obtaining image data. Further, the exemplary SEE probe(s) as described herein can be useful for imaging in locations traditional endoscope cannot access such as in hands, fingers, feet, and other body areas where a traditional probe is too large to fit.

In referring to the description, specific details are set forth in order to provide a thorough understanding of the examples disclosed. In other instances, well-known methods, procedures, components, and processes have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

More specific examples will be explained in the following embodiments.

Example 1

Probe. A first probe was formed using 0.66 NA multimode fibers (FSUA125145185). The outer diameters of this fiber are 125/145/185 µm for core/clad/coating, respectively. The coating diameter including max tolerance is 205 m. Smaller diameter 0.66 NA fibers could also be used to decrease probe diameter.

With detection of the signal, the output NA for high NA incidence into the detection fiber was found to be higher than that for low NA incidence on the fiber. (Output NA (13.5%) at 0.66 NA incidence is 0.32-0.47 while 0.25-0.30 at 0-degree incidence) and the output power for high NA incidence is lower than that for low NA incidence. (Output power at 0.66 NA incidence is less than 10% of that at 0-degree incidence.) Thus, there will be much smaller detection efficiency (probe and spectrometer) at high NA incidence than low NA incidence.

Spectrometer.

A spectrometer model, using estimated lens data from a 35 mm F/1.4 lens, provided a magnification of 0.35 and Hamamatsu sensor height of 500 µm. Thus, the height of fiber array which can be coupled to spectrometer is 500/0.35=1428 µm. With coated fibers as input, 7-8 fibers can be coupled into a fiber ring, and 9-10 fibers can be coupled into a fiber ring if the fibers are stripped.

In this design, the number of pixels of the sensor (pixel width=24 µm) corresponding to 450-820 nm light is 734. The number of resolvable points of monochromatic forward view probe is 302 in Rayleigh criteria, and 357 in Sparrow criteria with Gaussian beam at truncated $1/e2$ power. Therefore, sampling theorem is satisfied.

Example 2

A probe as described herein was fabricated and tested. The probe uses a 350 µm GRIN lens attached to a 500 µm spacer with one mirrored surface and one stamped epoxy grating. Collection optics include 16 multi-mode fibers arranged in a ring, circularly around the edge of the probe tip.

Figure 7A:
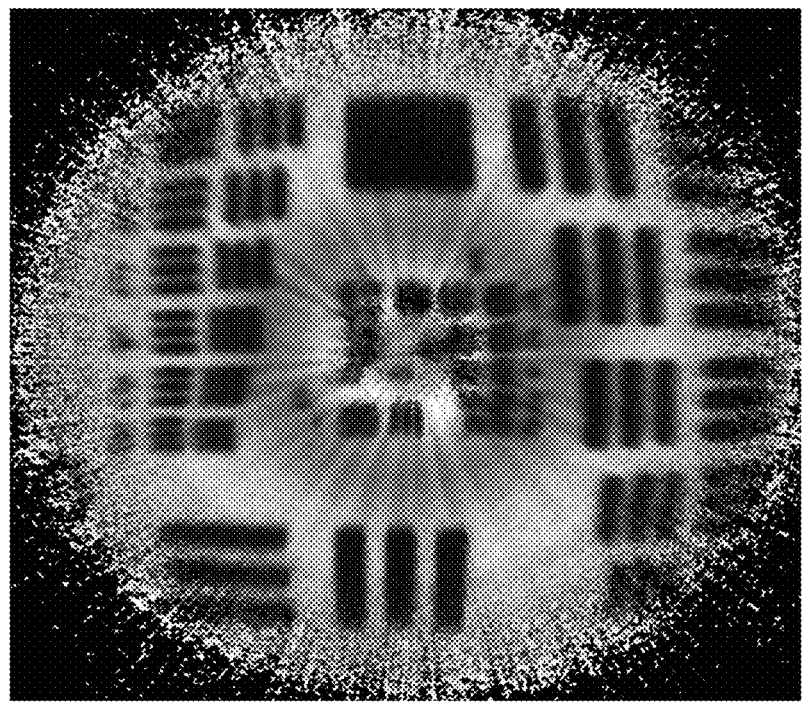
FIG. 7(A) is an exemplary image from a probe (circular conversion).
Figure 7B:
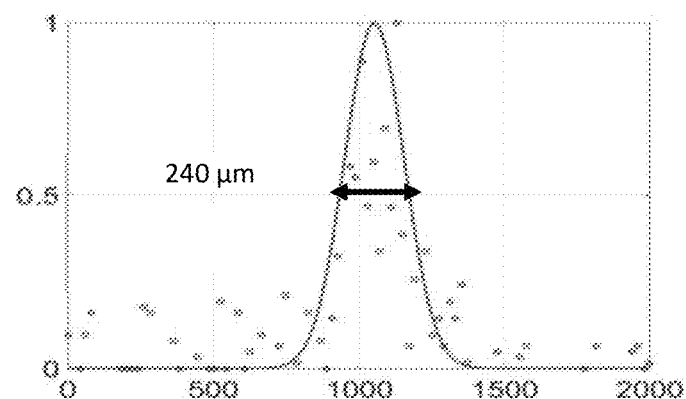
FIG. 7(B) is the LSF in the spectrally encoded direction with a FWHM of 240 µm and FIG. 7(C) is the LSF in the scanning direction with a FWHM of 167 µm
Figure 7C:
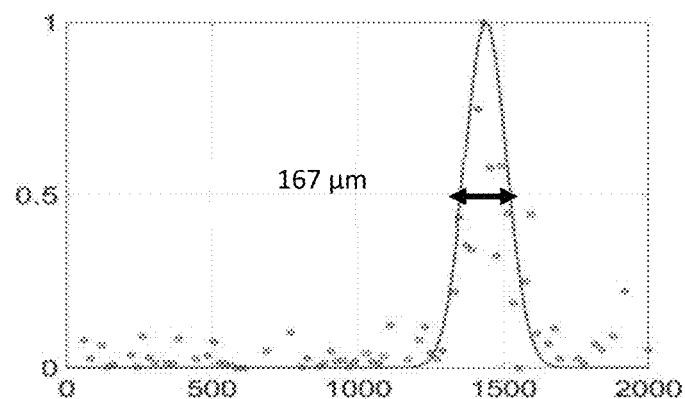

The fabricated probe had a 6-mm rigid length and an outer diameter of 500 µm. The line scan camera of this example has a pixel size of 24 µm×500 µm. FIG. 7(A) is an image taken with this probe. This probe was shown to have a 520 field-of-view angle with 148 resolvable points per diameter and 68,800 equivalent pixels per circular image. The imaging speed for one circular image was up to 15 fps imaging speed. An image made by this fiber-based probe is shown in FIG. 7(A). The line spread function (LSF) for the spectrally encoded direction was calculated to be 240 µm and the LSF in the scanning direction was calculated to be 167 µm. (See FIGS. 7(B) and 7(C). The probe itself can be seen in FIG. 8(A) and FIG. 8(B).

Example 3

A probe including a plurality of multimode detection fibers in a ring around the illumination optics having an outer diameter of 500 µm and surrounded by a polyimide tubing (ID 561 µm, OD 635 µm) was made by the following process:

Put the hypotubing (OD 650 m) into the stationary polyimide tubing (ID 700 µm, OD 800 µm). The hypotubing is used as a mandrel during the heat-shrink process to keep the shape of the stationary polyimide tubing, Place multi-mode fibers (OD 185 µm) on a sheet. Fix each fiber using a tape, Roll the fiber sheet around the stationary polyimide tubing, Place the fibers and tubings into the heat shrink tubing (recovered ID 686 µm) removing the tape, Check sheath end by stereomicroscope. Heat shrink tubing should be a little behind from ends of fibers and polyimide tubing, Apply heat to heatshrink the tubing by heat gun, Polish only fibers and polyimide tubings.

Replace the hypotubing with SEE illumination optics.

Figure 8A:
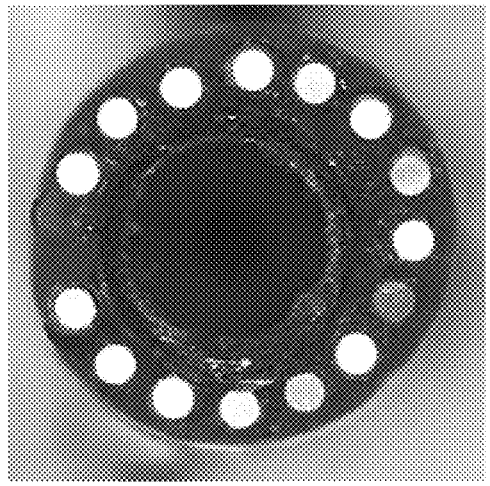
FIG. 8(A) is an image of a probe tip showing the distal end.
Figure 8B:
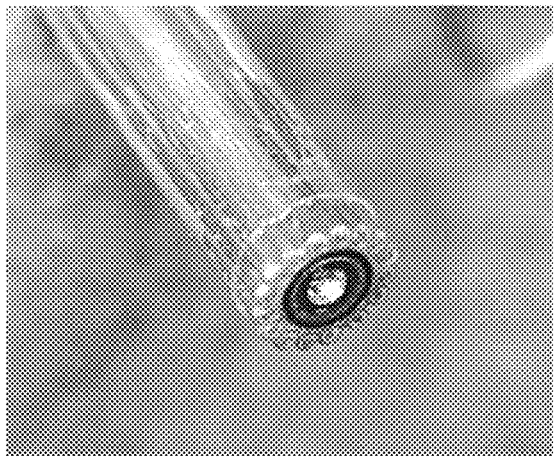
FIG. 8(B) is an image of the probe tip taken at an angle.

This process is shown in FIGS. 6(A) and 6(B). A probe was made having 15 fibers and is shown in FIGS. 8(A) and 8(B). In this embodiment, the MMF were not stripped. The sheath outer diameter was about 1.3 mm.

To use a single row of fibers for the spectrometer input, 8 of the 16 fibers in the probe (every other fiber in circular arrangement) were connected to spectrometer. (Sensor height=500 µm, spectrometer magnification=0.35, so the object height which can be coupled to the sensor is 1428 µm. This corresponds to a height of a row of 8 non-stripped fibers.) At spectrometer input, 8 MMFs were aligned in 1 vertical row. Light from the 8 fibers was coupled to the 500 µm-height sensor (Hamamatsu S11490 CCD sensor). DAQ from the spectrometer and RJ motor were set to have almost same speed and are preferably synchronized.

The image obtained using this system contained eight radial shadows. Since 8 of the 16 detection fibers were used, it is postulated that detection efficiency changes periodically in circumferential direction and causes the shadows.

Example 4

A miniaturized endoscope with diameter less than 1 mm, which has the potential to greatly reduce trauma and complications during internal imaging and treatment procedures, has been made. Broadband light (460-720 nm) was delivered to illumination optics through a single mode fiber. Inside the illumination optics, light was focused by a miniature GRIN lens (diameter=350 µm), reflected by a mirror surface (angle-polished surface of a 500-µm-diameter glass rod), and incident on a miniature grating (1379 lpmm). The incident angle on the grating was carefully chosen so that the shortest wavelength of the spectrum propagated along the optical axis of the illumination optics.

Two-dimensional illumination was accomplished by rotating the illumination optics at a rotation speed of 15 rps (revolution per second) using a miniature torque coil (diameter=560 µm). Reflected light from the sample was collected by a circular array of 16 multimode fibers (NA=0.66; diameter=185 µm). On the proximal side, the circular fiber array was rearranged to form a linear fiber array and light from the linear array was detected by a custom spectrometer with a tall-pixel camera (1024 pixels). The size of the final device inclusive of the detection fiber array was 1.3 mm in diameter. The rigid length was 6.2 mm. The SEE probe achieved a field-of-view (FOV) angle of 52° and the total number of effective pixels was 71,000. SEE videos showed that this technology enables endoscopic-like visualization of biological and non-biological samples. Thus there is provided a high-definition endoscopic that can image using a miniature forward-viewing SEE device.

Example 5

In another example, a miniaturized endoscope with diameter less than 1.3 mm, was used for imaging. Broadband light (415-784 nm) was delivered to illumination optics through a single mode fiber. Inside the illumination optics, light was focused by a miniature GRIN lens (diameter=250 µm), reflected by a mirror surface (angle-polished surface of a 500-µm-diameter glass rod), and incident on a miniature grating (2000 lpmm). The incident angle on the grating was carefully chosen so that the shortest wavelength of the spectrum propagated along the optical axis of the illumination optics. Two-dimensional illumination was accomplished by rotating the illumination optics at a rotation speed of 15 rps using a miniature torque coil (diameter=560 µm). Reflected light from the sample was collected by a circular array of 16 multimode fibers (NA=0.66; diameter=185 µm). As in the prior example, the circular fiber array was rearranged on the proximal side to form a linear fiber array and light from the linear array was detected by a custom spectrometer with a tall-pixel camera (1024 pixels). The size of the final device inclusive of the detection fiber array was 1.3 mm in diameter. The rigid length was 4 mm.

Figure 9A:
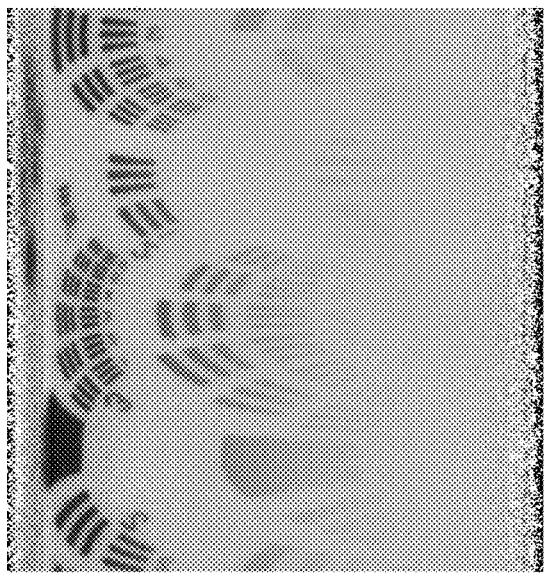
FIG. 9(A) shows the image with the initial rectangular data and FIG. 9(B) shows the image after circular conversion.
Figure 9B:
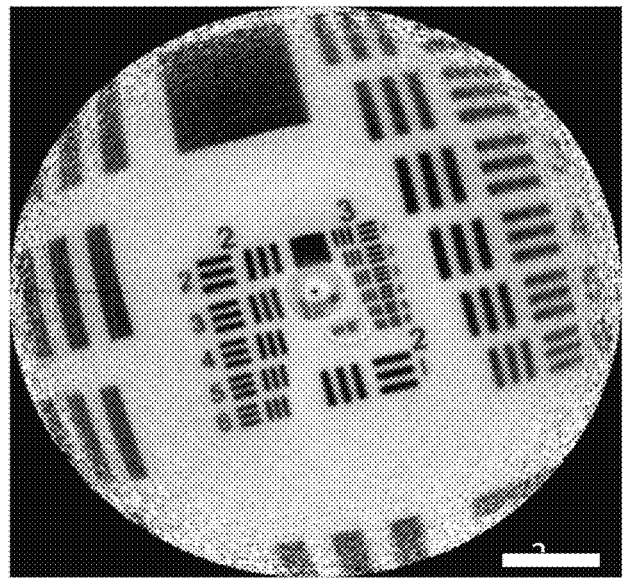

Imaging results from this probe are shown in FIG. 9 where the initial rectangular data is shown in FIG. 9(A), where FIG. 9(B) provides the same image after circular conversion. For the image of FIGS. 9(A) and 9(B), the FOV is 83 degree and the FWHM of LSF is 43.8 µm. For this image, there are 404 resolvable points, which corresponds to 513,000 pixels in the circular image. Spot size measurements provide:

| WD (mm) | Radial (µm) | Tangential (µm) |
| --- | --- | --- |
| 5 | 30.3 | 71.9 |
| 7.5 | 40.5 | 60.6 |
| 10 | 67.7 | 58.3 |

What is claimed is:

1. A probe having a proximal end and a distal end, and configured for spectrally encoded endoscopy (SEE) imaging, comprising:
    an illumination element comprising: a light guiding component; a first light focusing component; and a first dispersive component, arranged in this order along a probe axis from the proximal end to the distal end thereof; and
    a detection element comprising: a plurality of light collecting components; a second dispersive component; and a second light focusing component,
    wherein the illumination element is configured to rotate around the probe axis while the plurality of light collecting components remains stationary relative to the rotatable illumination element,
    wherein the distal ends of the plurality of light collecting components are arranged in a circle around the distal end of the illumination element to at least partially surround the first dispersive component, and
    wherein the proximal ends of the plurality of light collecting components form a linear array that is optically connected to the second dispersive component.

2. The probe of claim 1, wherein the plurality of light collecting components are multi-modal (MM) optical fibers.

3. The probe of claim 2, wherein the plurality of MM optical fibers comprises at least six MM optical fibers.

4. The probe of claim 2, wherein the distal ends of the plurality of MM optical fibers form a ring around the illumination element.

5. The probe of claim 2, wherein the numerical aperture of the plurality of MM optical fibers covers the entire field of view of the illumination element.

6. The probe of claim 1, further comprising a rotary junction configured to rotate the illumination element relative to the detection element.

7. The probe of claim 6, wherein the detection element is not rotated by the rotary junction.

8. The probe of claim 1, further comprising:
    a rotating tube having the illumination element fixedly arranged thereinside; and
    a non-rotating tube having the plurality of light collecting components fixedly attached to the outer surface thereof,
    wherein the rotating tube and the non-rotating tube are arranged coaxially between the illumination element and the plurality of light collecting components.

9. The probe of claim 1, wherein the second dispersive component is a spectrometer.

10. The probe of claim 9, wherein the linear array corresponds to an entrance slit of the spectrometer.

11. The probe of claim 1, wherein the detector is a line scan sensor.

12. The probe of claim 11, wherein the line scan sensor comprises rectangular pixels with the longer dimension of the rectangular pixels perpendicular to a grating vector of the second dispersive component.

13. An endoscopic imaging system, comprising:
    a light source;
    an illumination element configured to illuminate a sample;
    a detection element configured to collect light from the sample;
    a rotary junction configured to rotate the illumination element relative to the detection element;
    a detector configured to detect light collected by the detection element; and
    a processor configured to process data from the detector to form an image,
    wherein the illumination element and the detection element are arranged in a probe having a proximal end and a distal end, the illumination element comprising: a light guiding component, a first light focusing component, and a first dispersive component; arranged along the probe axis in this order from the proximal end to the distal end, the detection element comprising: a plurality of light collecting components; a second dispersive component; and a second light focusing component, wherein the illumination element is configured to rotate around the probe axis while the plurality of light collecting components remains stationary relative to the rotatable illumination element, wherein the proximal ends of the plurality of light collecting components form a linear array that is optically connected to the second dispersive component, and wherein the distal ends of the plurality of light collecting components are arranged in a circle around the distal end of the illumination element to at least partially surround the first dispersive component.

14. The imaging system of claim 13, wherein the plurality of light collecting components are multi-modal (MM) optical fibers.

15. The imaging system of claim 14, wherein the plurality of MM optical fibers comprises at least six MM optical fibers.

16. The imaging system of claim 14, wherein the distal ends of the plurality of MM optical fibers form a ring around the first dispersive component.

17. The imaging system of claim 14, wherein the numerical aperture of the plurality of MM optical fibers covers the entire field of view of the illumination element.

18. The imaging system of claim 13, further comprising:
a rotating tube having the illumination element fixedly arranged thereinside; and
a non-rotating tube having the plurality of light collecting components fixedly attached to the outer surface thereof,
wherein the rotating tube and the non-rotating tube are arranged coaxially between the illumination element and the plurality of light collecting components.

19. The imaging system of claim 13, wherein the second dispersive component is a spectrometer.

20. The imaging system of claim 19, wherein the linear array corresponds to an entrance slit of the spectrometer.

21. The imaging system of claim 13, wherein the detector is a line scan sensor comprising rectangular pixels with the longer dimension of the rectangular pixels perpendicular to a grating vector of the second dispersive component.

22. The imaging system of claim 13,
wherein the probe is a forward viewing SEE probe, and
wherein the first dispersive component is configured to diffract light such that at least one diffracted wavelength propagates substantially along the probe optical axis, where the probe optical axis is the axis extending along the direction of propagation of a light provided from the light guiding component through the first light focusing component.

23. The probe of claim 1,
wherein the probe is a forward viewing SEE probe, and
wherein the first dispersive component is configured to diffract light such that at least one diffracted wavelength propagates substantially along the probe optical axis, where the probe optical axis is the axis extending along the direction of propagation of a light provided from the light guiding component through the first light focusing component.

\* \* \* \* \*